US010603201B2

(12) United States Patent
Eriksson (10) Patent No.: US 10,603,201 B2
(45) Date of Patent: Mar. 31, 2020

(54) DYNAMIC JOINT STABILIZER (71) Applicant: DEROYAL GLOBAL HEALTHCARE SOLUTIONS LIMITED, Dublin (IE)

(72) Inventor: Thomas Eriksson, Bromma (SE)

(73) Assignee: DeRoyal Global Healthcare Solutions Limited (IE)

( * ) Notice: Subject to any disclaimer, the term of this patent is extended or adjusted under 35 U.S.C. 154(b) by 1171 days.

(21) Appl. No.: 14/394,201

(22) PCT Filed: Apr. 18, 2013

(86) PCT No.: PCT/EP2013/058074
§ 371 (c)(1),
(2) Date: Oct. 13, 2014

(87) PCT Pub. No.: WO2013/156561
PCT Pub. Date: Oct. 24, 2013

(65) Prior Publication Data
US 2015/0057588 A1 Feb. 26, 2015

(30) Foreign Application Priority Data

Apr. 20, 2012 (SE) ...................................... 1250395

(51) Int. Cl.
*A61F 5/01* (2006.01)
*A61F 5/37* (2006.01)
*A61F 13/14* (2006.01)

(52) U.S. Cl.
CPC ............ *A61F 5/013* (2013.01); *A61F 5/0104* (2013.01); *A61F 5/0118* (2013.01);
(Continued)

(58) Field of Classification Search
CPC .. A61F 5/00; A61F 5/01; A61F 5/0102; A61F 5/0104; A61F 5/0111;
(Continued)

(56) References Cited

U.S. PATENT DOCUMENTS

| 4,598,703 A | 7/1986 | Lindemann |
| 5,181,906 A | 1/1993 | Bauerfeind |

(Continued)

FOREIGN PATENT DOCUMENTS

WO    0049982    8/2000

OTHER PUBLICATIONS

PRV Patent-OCH Registreringsverket, Communication with a request for translation, dated Nov. 9, 2012, Translation of Office Action, Patent Application 1250395-9.
(Continued)

*Primary Examiner* — Keri J Nelson
(74) *Attorney, Agent, or Firm* — Luedeka Neely Group, PC (57) ABSTRACT

A reusable joint stabilizer for application to a joint of a patient, the stabilizer including a web having a pattern selected to provide a desired stability and restriction in the range of motion of the joint, the web being securable about the joint of the patient and formed of a plurality of flexible and non-stretchable strips interconnected in a desired pattern and a plurality of non-adhesive and reusable flexible tacky strips aligned with and connected to at least selected ones of the non-stretchable strips for positioning adjacent to skin of the patient proximate the joint. The tacky strips transfer forces between the exterior of the web and the skin of the patient contacted by the tacky strips to provide a desired stability of the joint and a desired restriction in the range of motion of the joint.

13 Claims, 11 Drawing Sheets

(52) U.S. Cl.
CPC .......... *A61F 5/3723* (2013.01); *A61F 13/146* (2013.01); *A61F 2220/0008* (2013.01)

(58) Field of Classification Search
CPC ...... A61F 5/0118; A61F 5/0127; A61F 5/013; A61F 5/37; A61F 5/3723; A61F 2220/0008
USPC ...................... 602/20, 23, 27, 60–62, 78, 79
See application file for complete search history.

(56) References Cited

U.S. PATENT DOCUMENTS

| | | | |
|---|---|---|---|
| 5,628,725 | A | 5/1997 | Ostergard |
| 5,938,631 | A | 8/1999 | Colman |
| 6,106,493 | A | 8/2000 | Rozell |
| 6,398,746 | B2 | 6/2002 | Bramlage et al. |
| 6,440,094 | B1 | 8/2002 | Maas |
| 7,081,101 | B1 | 7/2006 | Sawa |
| 7,135,005 | B2* | 11/2006 | Kania .................... A61F 5/3738 602/19 |
| 7,452,343 | B2* | 11/2008 | Campbell ............. A61F 13/066 602/23 |
| D608,896 | S | 1/2010 | Arbesman et al. |
| D621,052 | S | 8/2010 | Kase |
| 7,785,281 | B2 | 8/2010 | Scott |
| 7,871,388 | B2* | 1/2011 | Brown .................... A61F 5/026 602/19 |
| 7,902,420 | B2 | 3/2011 | Kase |
| 2006/0070165 | A1 | 4/2006 | Nordt, III et al. |
| 2006/0167395 | A1 | 7/2006 | Sawa |
| 2007/0021706 | A1 | 1/2007 | Braunstein et al. |
| 2008/0208092 | A1 | 8/2008 | Sawa |
| 2008/0228118 | A1* | 9/2008 | Bull ...................... A61F 5/3723 602/16 |
| 2009/0259156 | A1 | 10/2009 | Nordt, III et al. |
| 2010/0049112 | A1 | 2/2010 | Protasiewicz et al. |
| 2010/0312160 | A1 | 12/2010 | Creighton et al. |
| 2012/0041352 | A1* | 2/2012 | Ostergard ............. A61F 5/3723 602/20 |

OTHER PUBLICATIONS

PRV Patent-OCH Registreringsverket, Office Action, dated Nov. 9, 2012.
Awapatent, Letter regarding International Search Report and Written Opinion, dated Aug. 6, 2013.
Patent-OCH Registreringsverket, Stockholm, Awapatent AB, May 8, 2013.
Active Forever Fitness Safety and Medical Supplies, Bauerfeind OmoTrain Shoulder Support, activeforever.com, p. 1532, Dec. 18, 2012.
Breg, Inc., Vista, California, Shoulder Stabilizer Instructions, The date of this photo is not known, but it is requested that it be considered as prior art for purposes of examination.
Med Supports, Thermoskin Sport Shoulder Support, Dec. 18, 2012 medsupports.com.
Djo, LLC, Donjoy Patellofemoral Bracing, Reaction Knee Brace, Nov. 9, 2011 donjoy.com.
EVS Sports, SB04 Shoulder Brace, Dec. 12, 2012 evs-sports.com healthykin.com, Thermoskin Sports Shoulder Universal 84130, Feb. 3, 2012, healthykin.com.
Djo Global, Donjoy, Sully Shoulder Stabilizer, Dec. 18, 2012, pulls the humerus posteriorly as it restricts external rotation and abduction djoglobal.com.
Djo Global, DonJoy, Sully Shoulder Stabilizer, Dec. 18, 2012 provides shoulder immobilization and controlled range of motion djoglobal.com.
Saunders Sully Shoulder Stabilizer, Sm 660087-002, Feb. 3, 2012, braceshop.com betterbraces.com.
Simmons Preston Rolyan, Rolyan MFC Unilateral Shoulder Orthosis, Rolyan MFC II Unilateral Shoulder Orthosis, 1992, Bolingbrook IL USA.
Bauerfeind USA, OmoTrain Active Support for early functional treatment of the shoulder joint, Dec. 18, 2012 bauerfeindusa.com.
McDavid USA, 462R McDavid Level 2 Shoulder Support, Dec. 18, 2012 mcdavidusa.com.
Breg The date of this photo is not known, but it is requested that it be considered as prior art for purposes of examination.
Donjoy Shoulder Stabilizer The date of this photo is not known, but it is requested that it be considered as prior art for purposes of examination.
Sully 1 The date of this photo is not known, but it is requested that it be considered as prior art for purposes of examination.
Sully 2 The date of this photo is not known, but it is requested that it be considered as prior art for purposes of examination.
Sully 3 The date of this photo is not known, but it is requested that it be considered as prior art for purposes of examination.
Sully 4 The date of this photo is not known, but it is requested that it be considered as prior art for purposes of examination.
EVS S5B03 Shoulder Brace The date of this photo is not known, but it is requested that it be considered as prior art for purposes of examination.
McDavid The date of this photo is not known, but it is requested that it be considered as prior art for purposes of examination.
MFC Shoulder The date of this photo is not known, but it is requested that it be considered as prior art for purposes of examination.
Omotrain Fitting Image The date of this photo is not known, but it is requested that it be considered as prior art for purposes of examination.
Omotrain The date of this photo is not known, but it is requested that it be considered as prior art for purposes of examination.
PCT International Search Report, PCT/EP2013/058074 dated Jul. 9, 2013.

* cited by examiner

DYNAMIC JOINT STABILIZER

CROSS-REFERENCE TO RELATED APPLICATION

This application claims priority under all applicable statutes, and is a U.S. National phase (37 U.S.C. Section 371) of International Application PCT/EP2013/058074, filed Apr. 18, 2013, and entitled DYNAMIC JOINT STABILIZER, which claims priority to SE 1250395-9, filed Apr. 20, 2012, incorporated herein by reference in their entireties.

FIELD

This disclosure relates to the field of joint stabilizers. More particularly, the disclosure relates to a dynamic joint stabilizer.

BACKGROUND

Taping is often used to stabilize a body joint, such as the shoulder joint, and to enable a limited range of motion of the joint. Stabilization of a body joint may be indicated in the event of injury or following a surgical procedure. It is believed that taping can provide both mechanical and proprioceptive effects to the joint that are beneficial to rehabilitation of the joint.

Taping desires improvement, as the taping must be re-applied and is otherwise inconvenient for use on a repeated basis. In addition, the use of tape for a prolonged period can be detrimental to the skin of the user. Also, some patients have skin reactions to tape.

Accordingly, the present disclosure relates to an improved joint stabilizer that can stabilize the joint and limit the range of motion of the joint in the manner of taping, but which is reusable and avoids many of the shortcomings associated with taping.

SUMMARY

The disclosure relates to a reusable joint stabilizer. In one aspect, the stabilizer includes a web having a pattern selected to provide a desired stability and restriction in the range of motion of the joint, the web being securable about the joint of the patient and formed of a plurality of flexible and non-stretchable strips interconnected in a desired pattern and a plurality of non-adhesive and reusable flexible tacky strips aligned with and connected to at least selected ones of the non-stretchable strips for positioning adjacent to skin of the patient proximate the joint.

The tacky strips transfer forces between the exterior of the web and the skin of the patient contacted by the tacky strips to provide a desired stability of the joint and a desired restriction in the range of motion of the joint.

In another aspect, an elastic textile material such as neoprene is combined with the web to provide compression, heat retention, and other effects.

Joint stabilizers according to the disclosure may be applied to a joint of the user to provide stability to the joint and a desired restriction in the range of motion of the joint. It is believed that the web functions in the manner of taping and enables both mechanical and proprioceptive effects to the joint that are beneficial to rehabilitation of the joint. However, the web advantageously may be removed and re-applied repeatedly and avoids disadvantages associated with taping.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
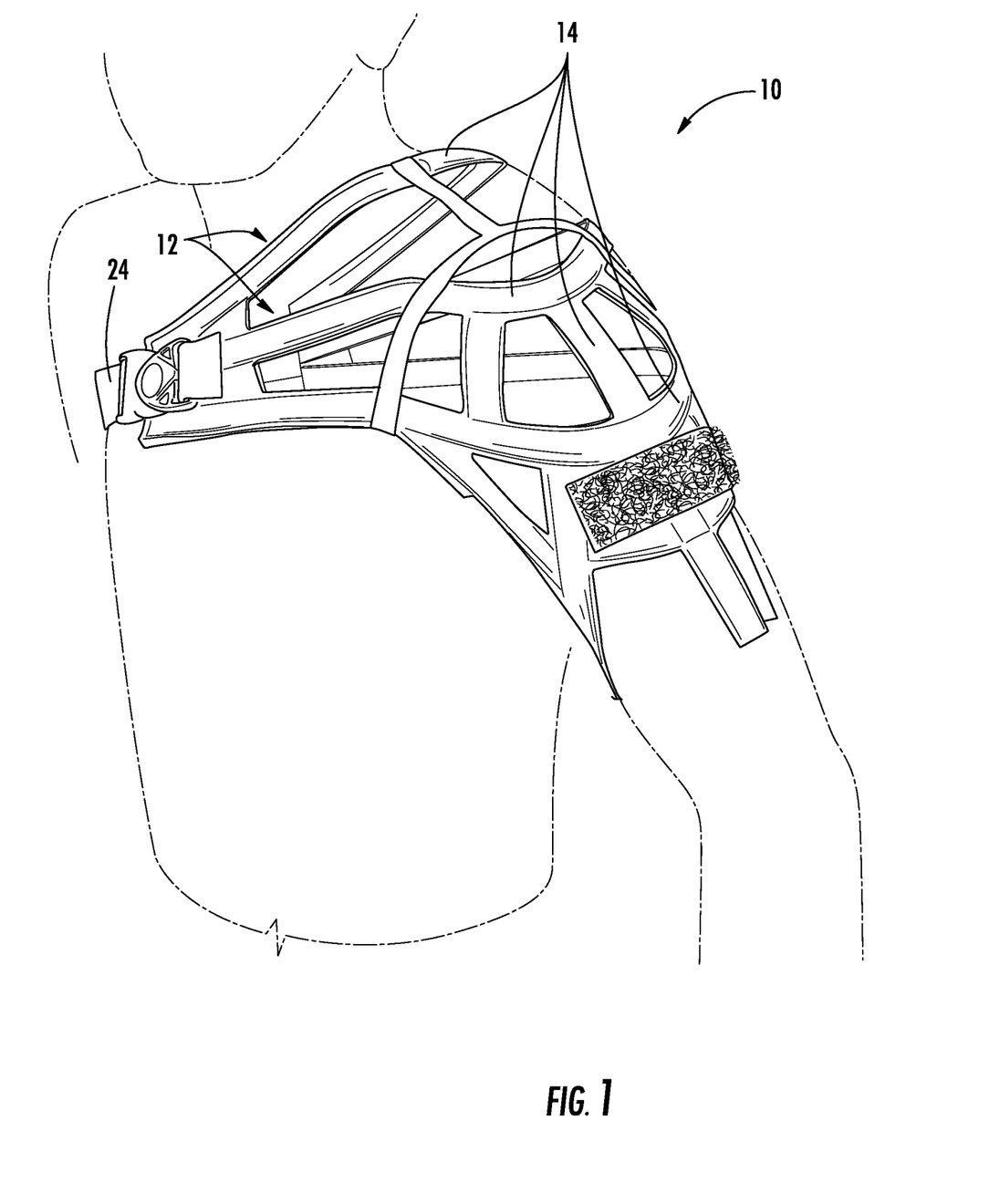
FIG. 1 is a perspective view showing a joint stabilizer according to the disclosure applied to a shoulder joint.
Figure 2:
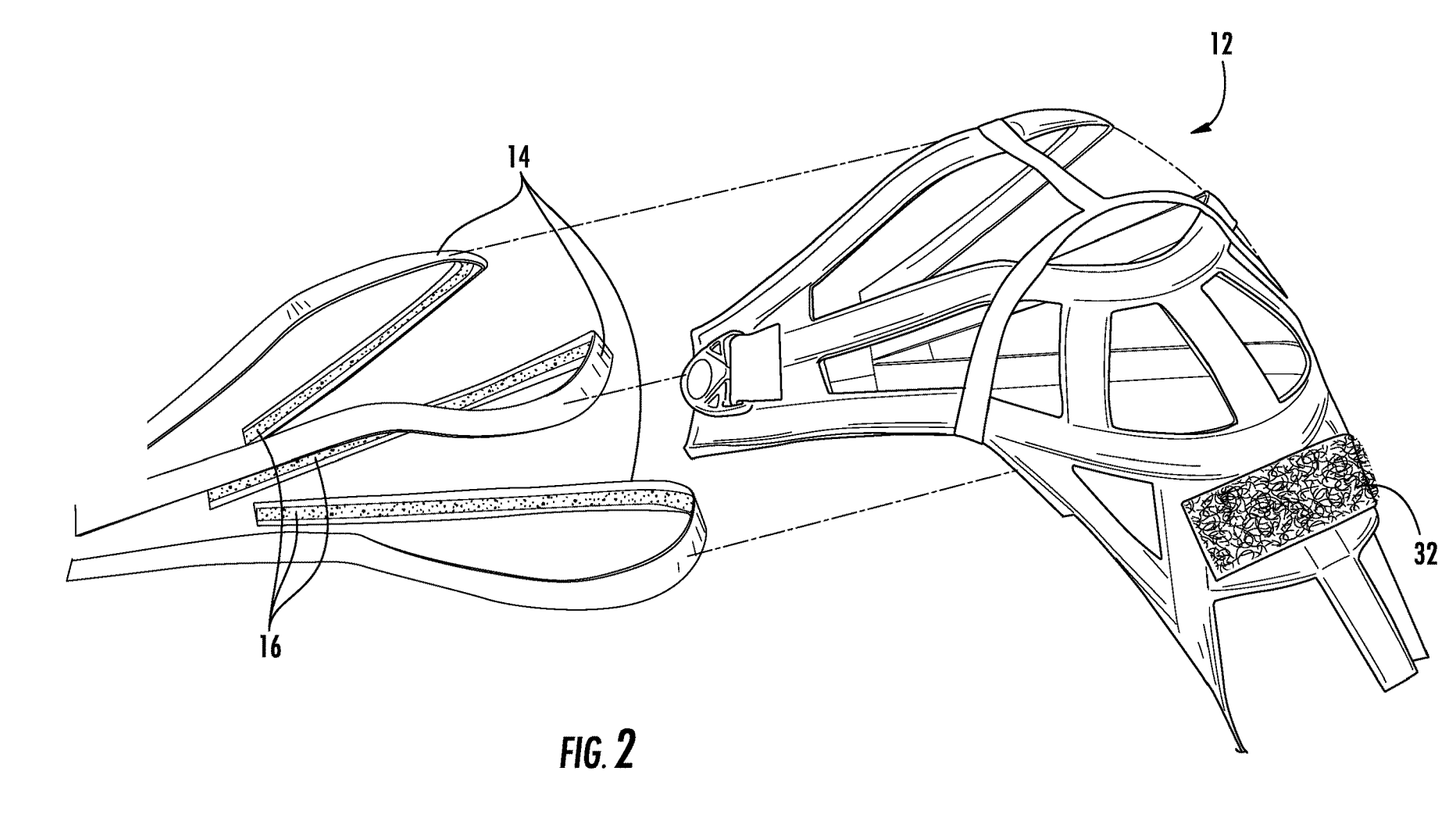
FIG. 2 shows portions of the stabilizer of FIG. 1 exploded so as to show tacky strips applied to non-stretchable strips of the stabilizer.

With reference to the drawings, and initially to FIGS. 1 and 2, the disclosure relates to a joint stabilizer 10 having a web 12 formed of a plurality of flexible but substantially non-stretchable strips 14 interconnected in a desired pattern or arrangement depending on the desired effect. A plurality of non-adhesive and reusable flexible tacky strips 16 are located on the interior of the web 12 and aligned with and connected to at least selected ones of the non-stretchable strips 14.

As used herein, the term "non-adhesive" will be understood to refer to distinguish from adhesive strips such as tape or the like having a backing material coated with an adhesive. Likewise, it will be understood that tape is generally not reusable in that it cannot be repeatedly installed, uninstalled, and re-installed. Reusable as used herein refers to substantially unlimited re-use within the context of a patient wearing a joint stabilizer according to the disclosure for an extended period of time commensurate with treatment of the joint. With regard to the "non-stretchable" terminology, it will be understood that the strips 14 are flexible and have some dimensional instability, but substantially maintain their length and width dimensions absent tearing or rupture.

The flexible and non-stretchable strips 14 may be provided as by strips of synthetic leather. The flexible tacky strips 16 may be provided by soft silicone strips.

The pattern or arrangement of the web 12 is selected to provide a desired stability and restriction in the range of motion of the joint. It has been observed that the tacky strips 16 transfer forces between the exterior of the web 12 and the skin of the patient contacted by the tacky strips 16. The tacky strips 16 may be connected to the non-stretchable strips 14 as by stitches or manner of fastening, or co-formed therewith.

The transfer of force achieved by the combination of the web 12 of the non-stretchable strips 14 and the tacky strips 16 has been observed to provide a desired stability of the joint of the user and a desired restriction in the range of motion of the joint. It is believed that the web 12 functions in the manner of taping and enables both mechanical and proprioceptive effects to the joint that are beneficial to rehabilitation of the joint. However, the web 12 advantageously may be removed and re-applied repeatedly and avoids disadvantages associated with taping.

The depicted joint stabilizer 10 is configured to stabilize the shoulder joint. However, it will be appreciated that joint stabilizers according to the disclosure may be configured to stabilize various body joints, including the ankle, knee and wrist joints.

The stabilizer 10 may be configured to include additional straps and securement devices to maintain the stabilizer 10 in a desired position about the joint. In this regard, and with reference to FIGS. 3-5, there is shown an alternate embodiment of a joint stabilizer 20 that incorporates an elastic textile 22 with the non-stretchable strips 14 and the tacky strips 16. The stabilizer 20 is also configured to include a chest strap system 24 and a supplemental strap system 26 having a waist belt 28 and a supplemental strap 30.

Figure 3:
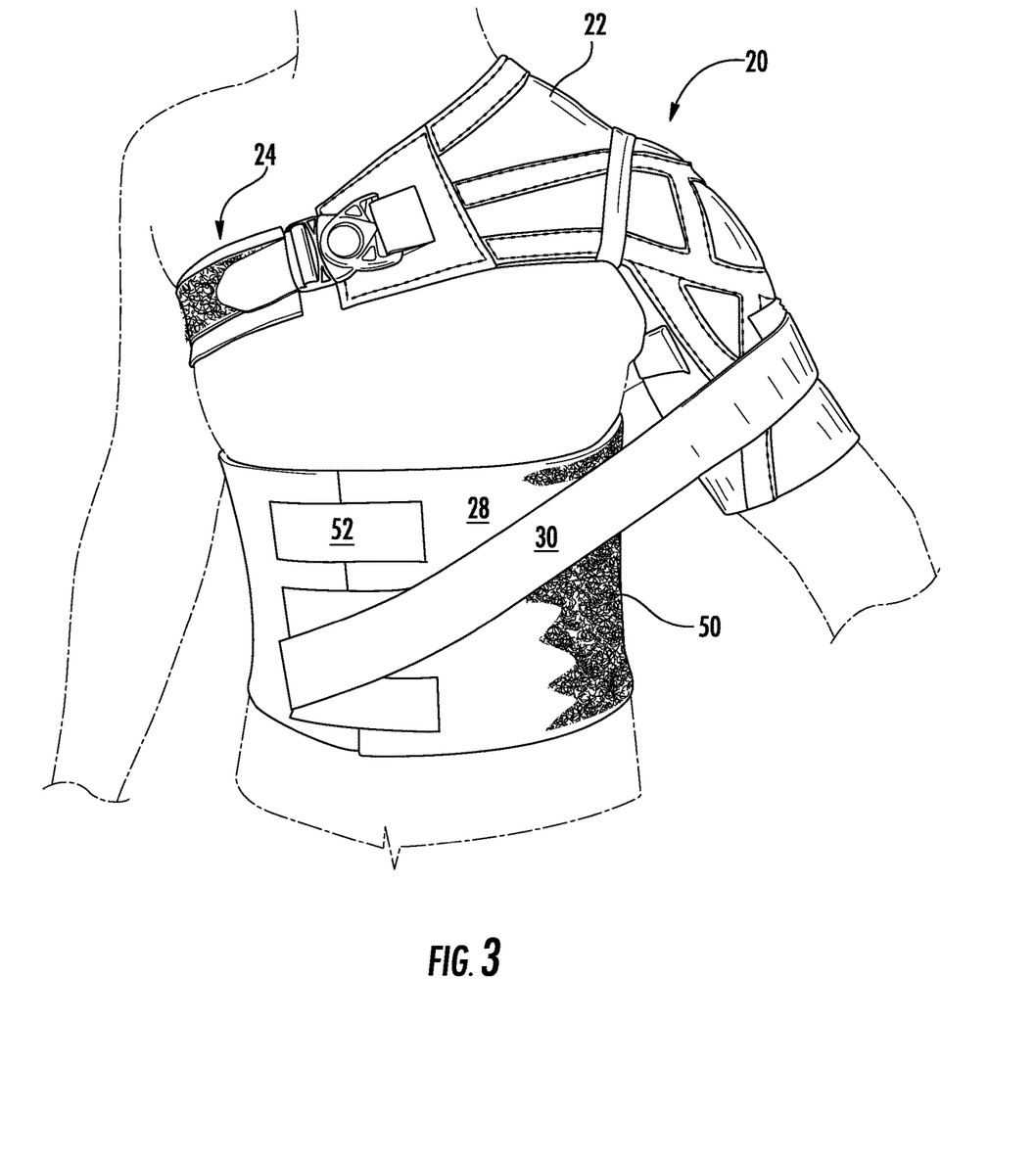
FIG. 3 shows a perspective view of an alternate embodiment of a joint stabilizer system according to the disclosure.
Figure 4:
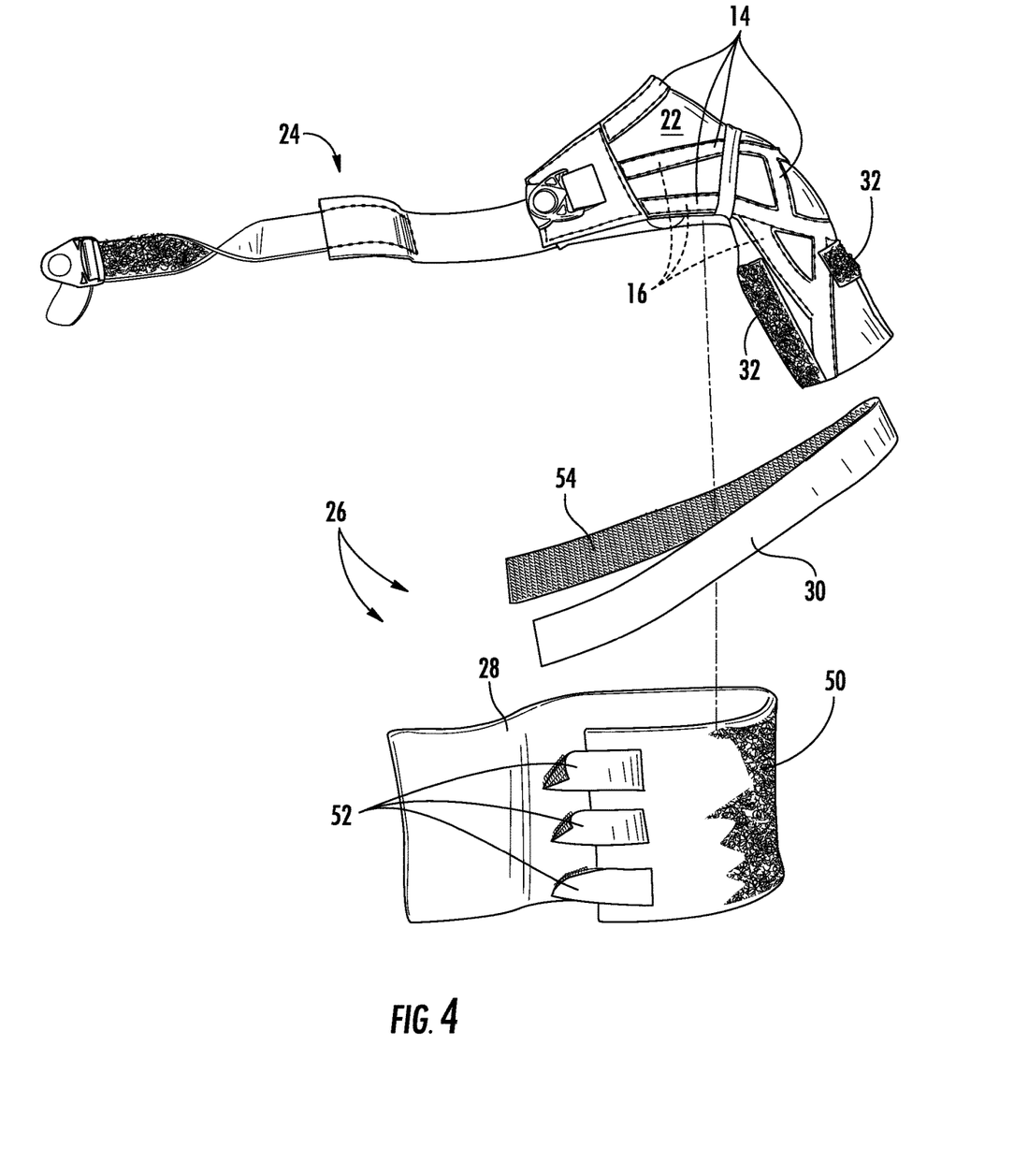
FIG. 4 is a partially exploded view of the joint stabilizer system of FIG. 3.
Figure 5:
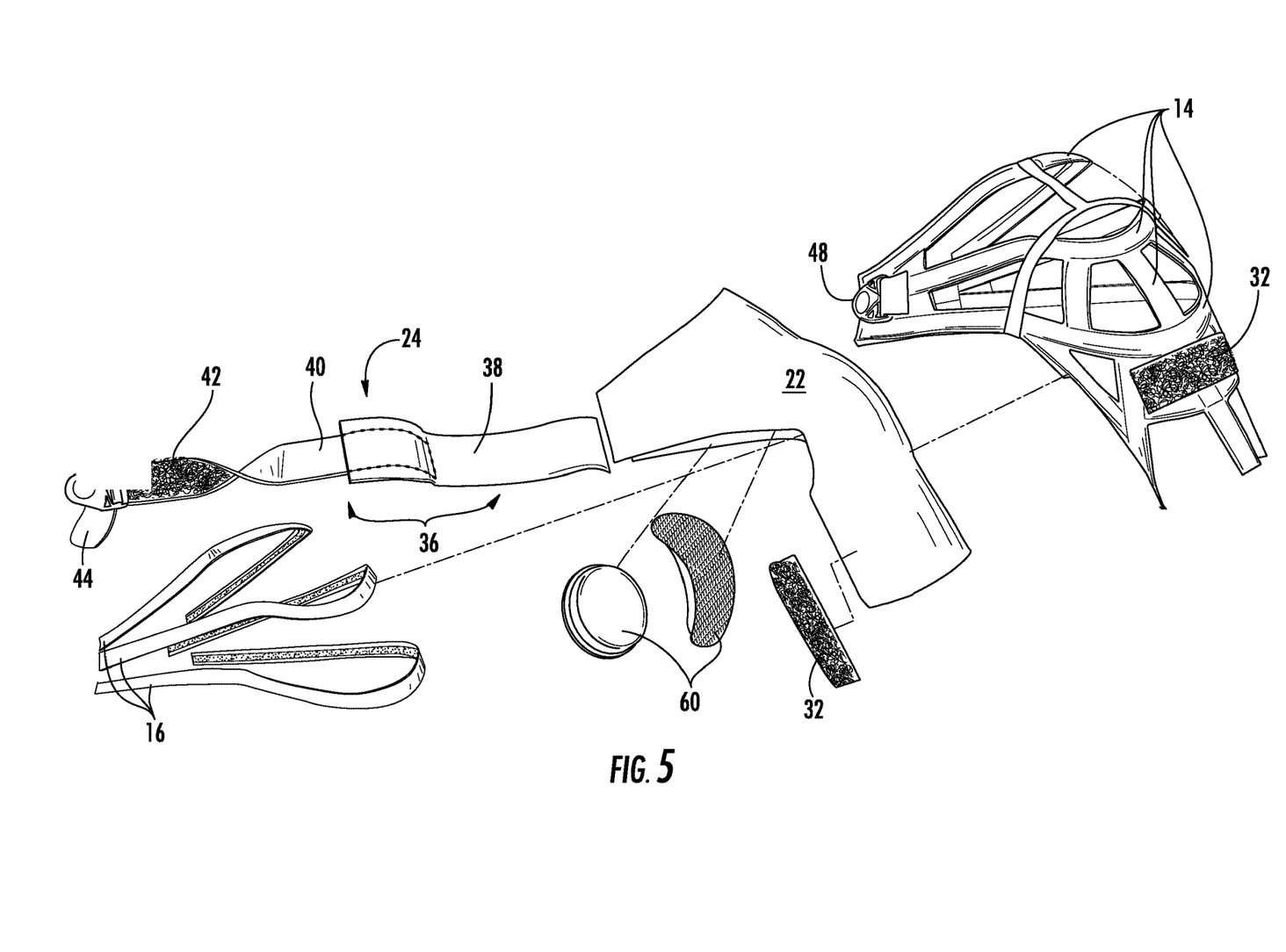
FIG. 5 is a further exploded view of the joint stabilizer system of FIG. 3.

The elastic textile 22 may be provided as by neoprene configured to fit about the shoulder joint to provide compression, heat retention, and other effects to the joint. The stabilizer 20 may be made by locating the web 12 formed of the non-stretchable strips 14 about the exterior of the elastic textile 22, with the tacky strips 16 adjacent the interior of the elastic textile 22 and aligned with and connected to at least selected ones of the non-stretchable strips 14. In this regard, the strips 14 and 16 may each be adhered to the elastic textile 22 which fixes the locations of the strips 14 and 16 and thereby interconnects them via their fixed locations on the elastic textile 22. However, it is preferred to utilize stitches or the like that extend through both the strips 14 and 16 and the elastic textile 22. In this regard, the stitches or other fastening devices are preferably configured to provide a smooth profile so as to not irritate the skin of the user. It has been observed that the stabilizer 20 provides anterior and posterior stability of the shoulder joint, with up to about 45 degree abduction.

To facilitate installation of the stabilizer 20 (and the stabilizer 10) to the user, the elastic textile 22 and/or the web 12 may include a hook or loop material, such as material 32, secured at desired locations thereon and securement straps 34 secured to the elastic material 22 and having loop or hook material thereon to releasably mate with the material 32. Likewise, it will be appreciated that other fastening devices, such as snaps, buttons, and the like may be utilized.

Figure 6:
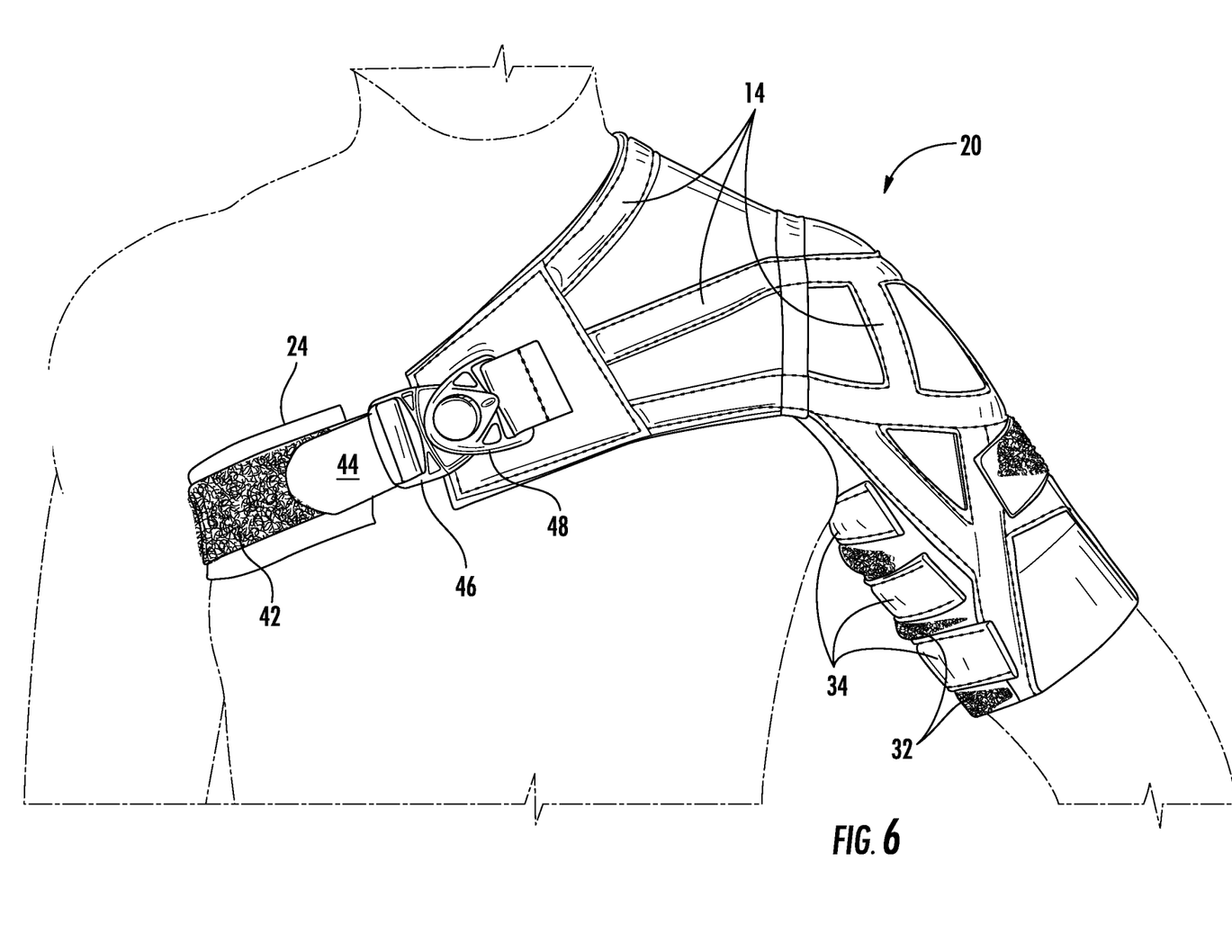
FIGS. 6 and 7 are front and rear plan views showing a strap system utilized with the joint stabilizer system of FIG. 3.
Figure 7:
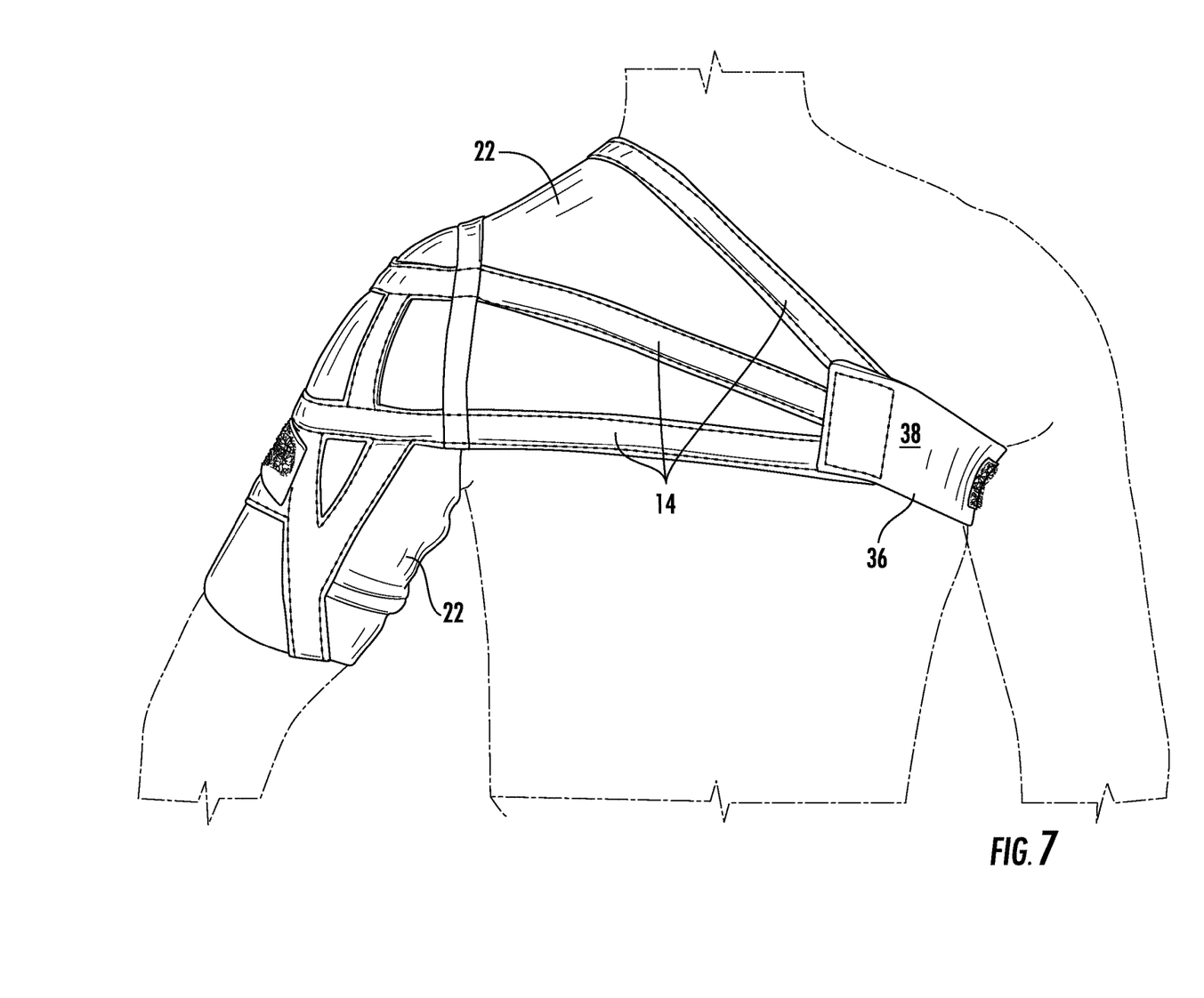

The strap system 24 includes a strap 36 that extends from the web 12 or the elastic textile 22 adjacent a rear of the stabilizer 10 or 20. The strap 36 includes an elastic section 38 made of an elastic textile material such as neoprene, representing about half of the length of the strap 36, and a non-stretchable section 40 having a loop material 42 provided thereon extends from the elastic section 38. The terminal end of the loop material has a section of hook material 44 secured thereto. It will be understood that the hook/loop material may be reversed in their locations so as to provide mating hook and loop material at the desired locations. A slide buckle 46 is adjustably positioned on the non-stretchable section 40 of the strap 35. A receiver 48 is secured to the web 12 for receiving the buckle 46. When the buckle 46 is received by the receiver 48, the hook material 44 may be engaged with the loop material 42 to fix the length of the strap 36.

The elastic section 38 of the strap 36 adds to the posterior stability of the shoulder as the compression in the elastic textile 22 when elongated will distribute forces to the strips 14 for transfer over the web 12. Since the front of the strap 36 is non-elastic, the strap 36 remains the elastic pull on the back portion of the strap 36 even when the buckle 46 is received by the receiver 48 and the hook material 44 is engaged with the loop material 42. Furthermore the elastic textile of the elastic section 38 has a skin gripping function which also secures the position of the strap 36. Thus, the installed and adjusted strap 36 tends to apply a counter force from the opposite side of the injured shoulder. This has been observed to add additional mechanical and proprioceptive effects to the joint that are beneficial to rehabilitation of the joint.

The supplemental strap system 26 having the waist belt 28 and the supplemental strap 30 may also be utilized to provide additional stability effects to the joint. For example, the use of the waist belt 28 and the supplemental strap 30 can be used to further limit the range of motion if desired. With reference to FIGS. 3 and 4, the waist belt 28 may be provided as by an elastic textile material, such as neoprene. To aid in securement of the belt 28 about the waist or chest of the user, the exterior of the belt 28 may include a loop (or hook) material 50 and straps 52 having a hook (or loop) material may be secured to the belt 28 for engaging the material 50. The supplemental strap 30 includes a hook (or loop) material 54 to facilitate attachment of the strap 30 to both the belt 28 and the stabilizer 20 (or stabilizer 10). That is, the strap 30 may be oriented to engage both the material 50 of the belt and the material 32 of the stabilizer 20 (or stabilizer 10). It will be understood that other fasteners may be utilized.

Features such as pads 60 may be included with the stabilizers 10 and 20. For example, the pads 60 may be adjustably positionable as desired between the stabilizer and the patient as by the use of mating hook and loop material or the like. The pads 60 can assist in supporting and stabilizing the joint by the additional selected compression they provide.

Figure 8:
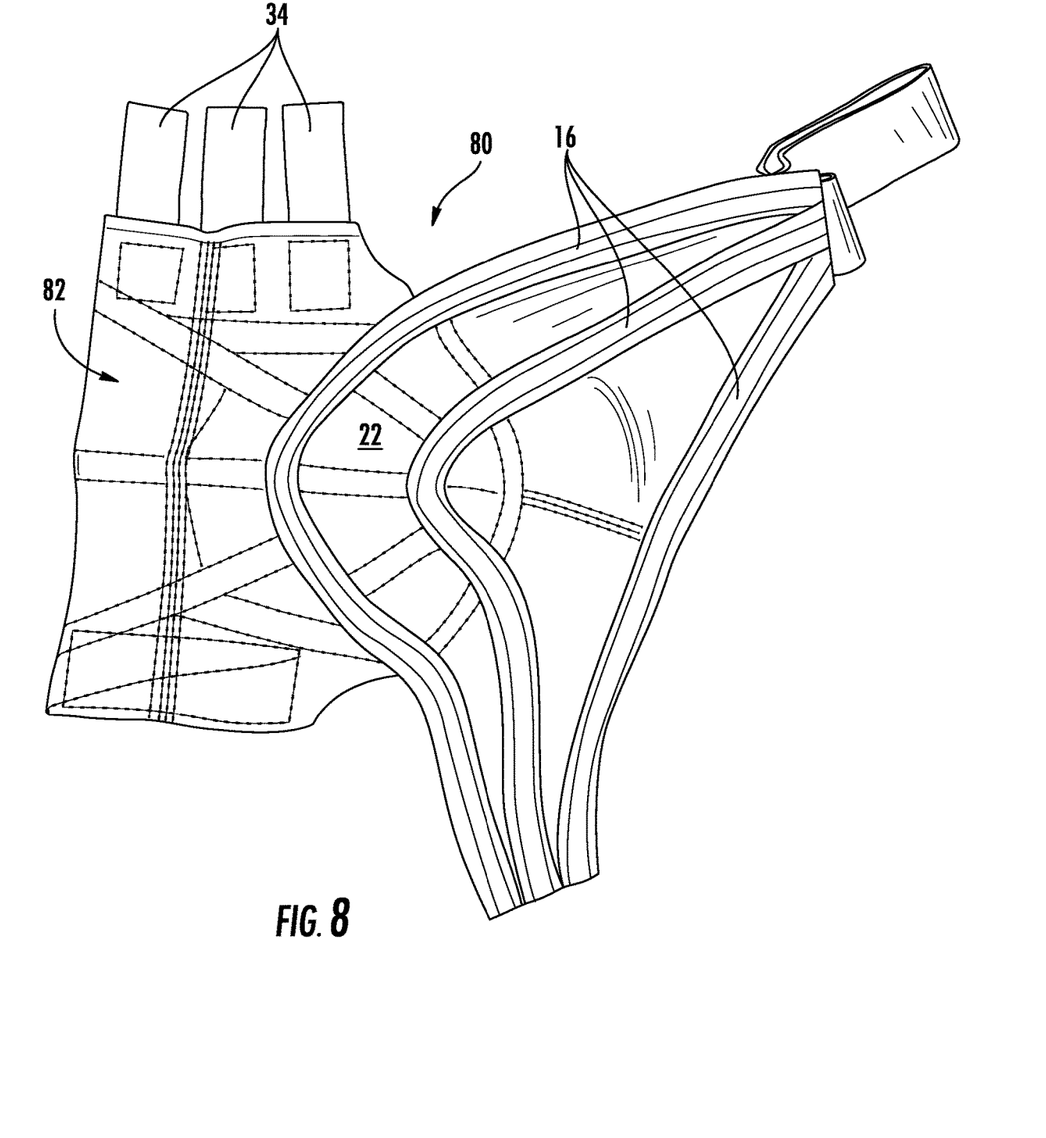
FIG. 8 shows an interior view of another shoulder stabilizer according to the disclosure.

With reference to FIG. 8, there is shown a stabilizer 80 according to the disclosure. The stabilizer 80 is substantially similar to the stabilizer 20. As will be observed, a distal portion of a sleeve structure 82 provided by the elastic textile 22 is able to contact and be tightened around the arm of the user by use of the securement straps 34. In this regard, it has been observed that the sleeve structure 82 substantially grips the arm and inhibits relative movement of the arm. This has been observed to advantageously also provide a suspension function to the upper arm.

Figure 9:
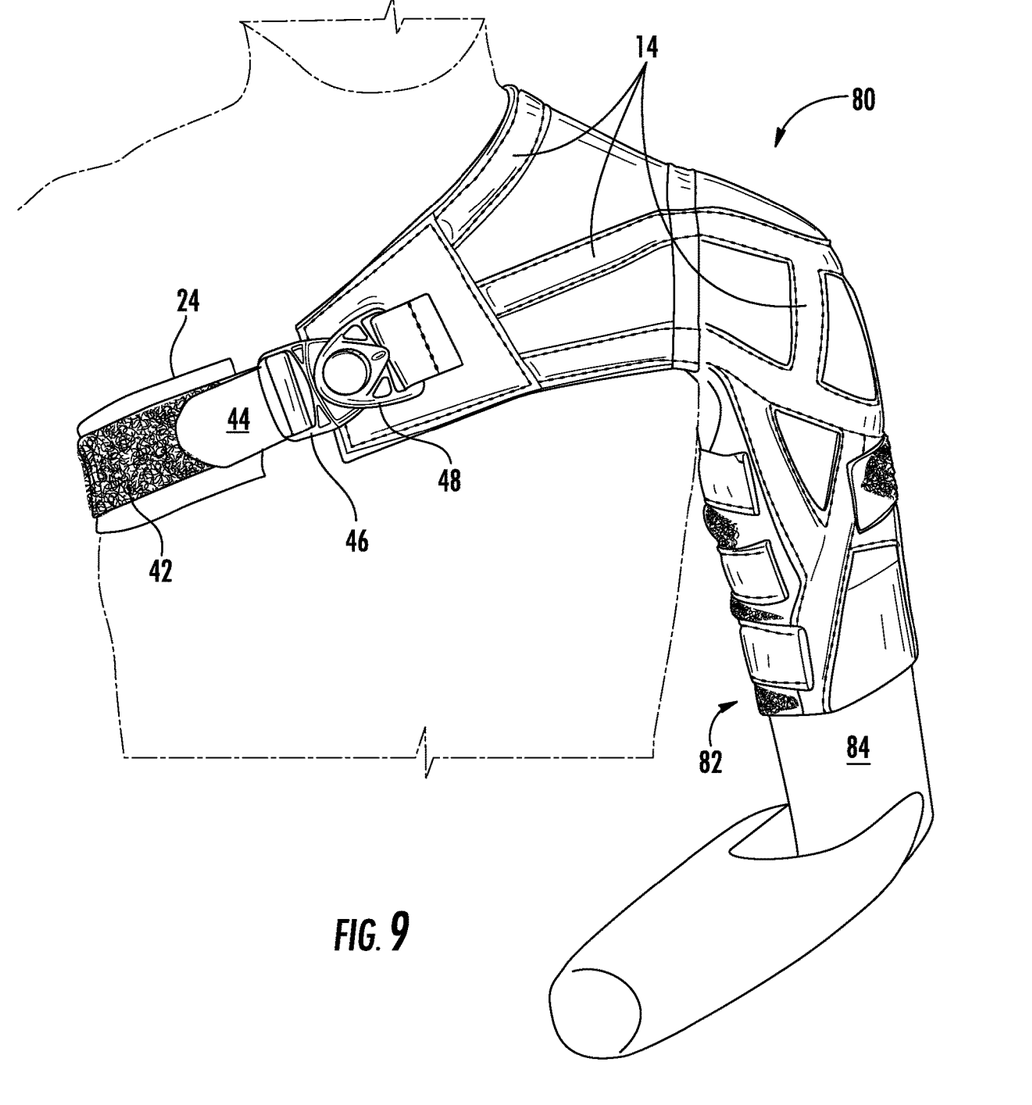
FIG. 9 shows the stabilizer of FIG. 8 utilized to help support and stabilize a prosthetic arm.

The described suspension function has been observed to be advantageous to help support the arm in the case of persons having shoulder injuries. In addition, it has been observed that this suspension feature may also be advantageous to support a prosthetic arm, such as prosthetic arm 84 shown in FIG. 9.

Figure 10:
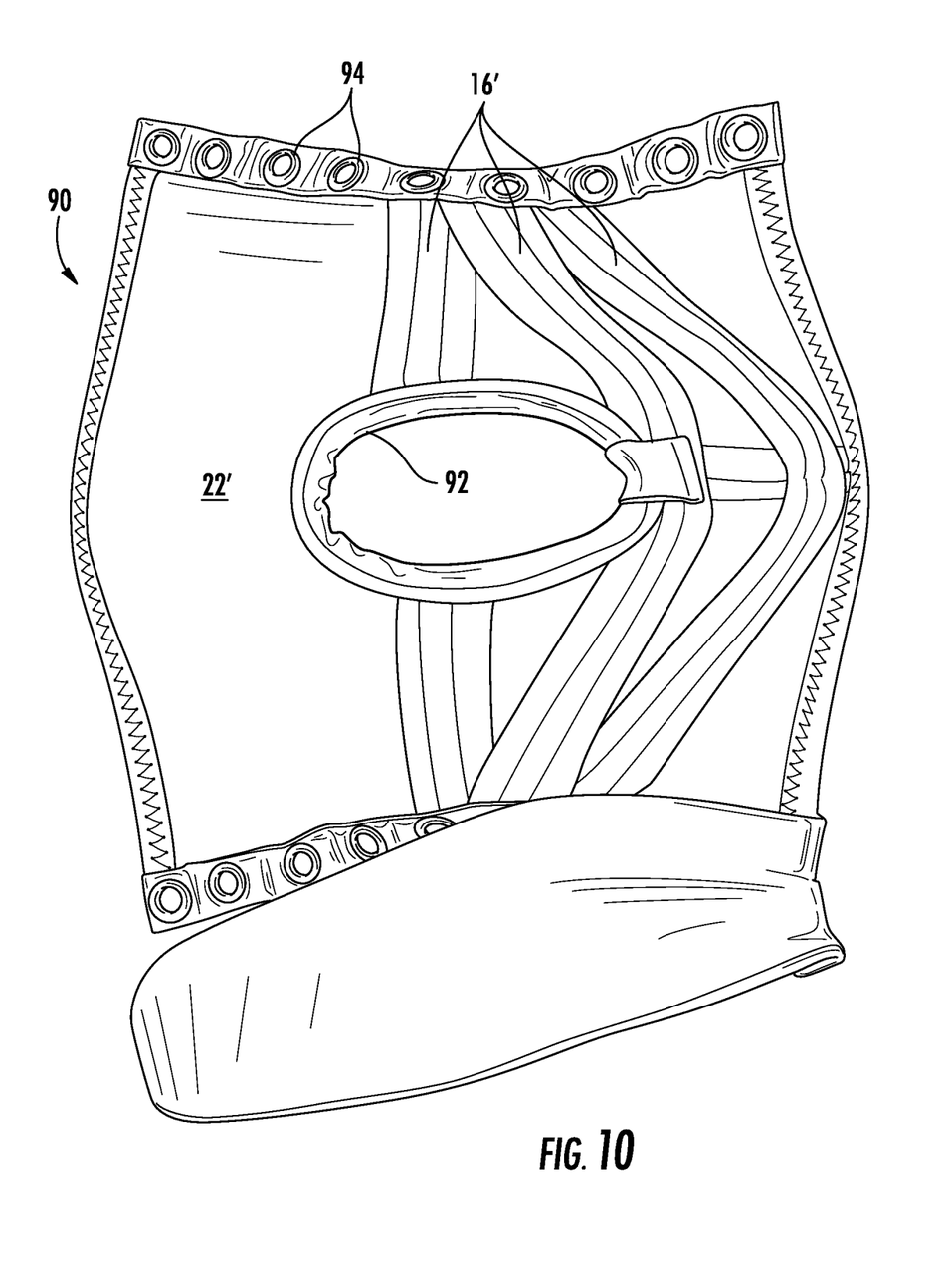
FIG. 10 shows an interior view of an ankle stabilizer according to the disclosure.
Figure 11:
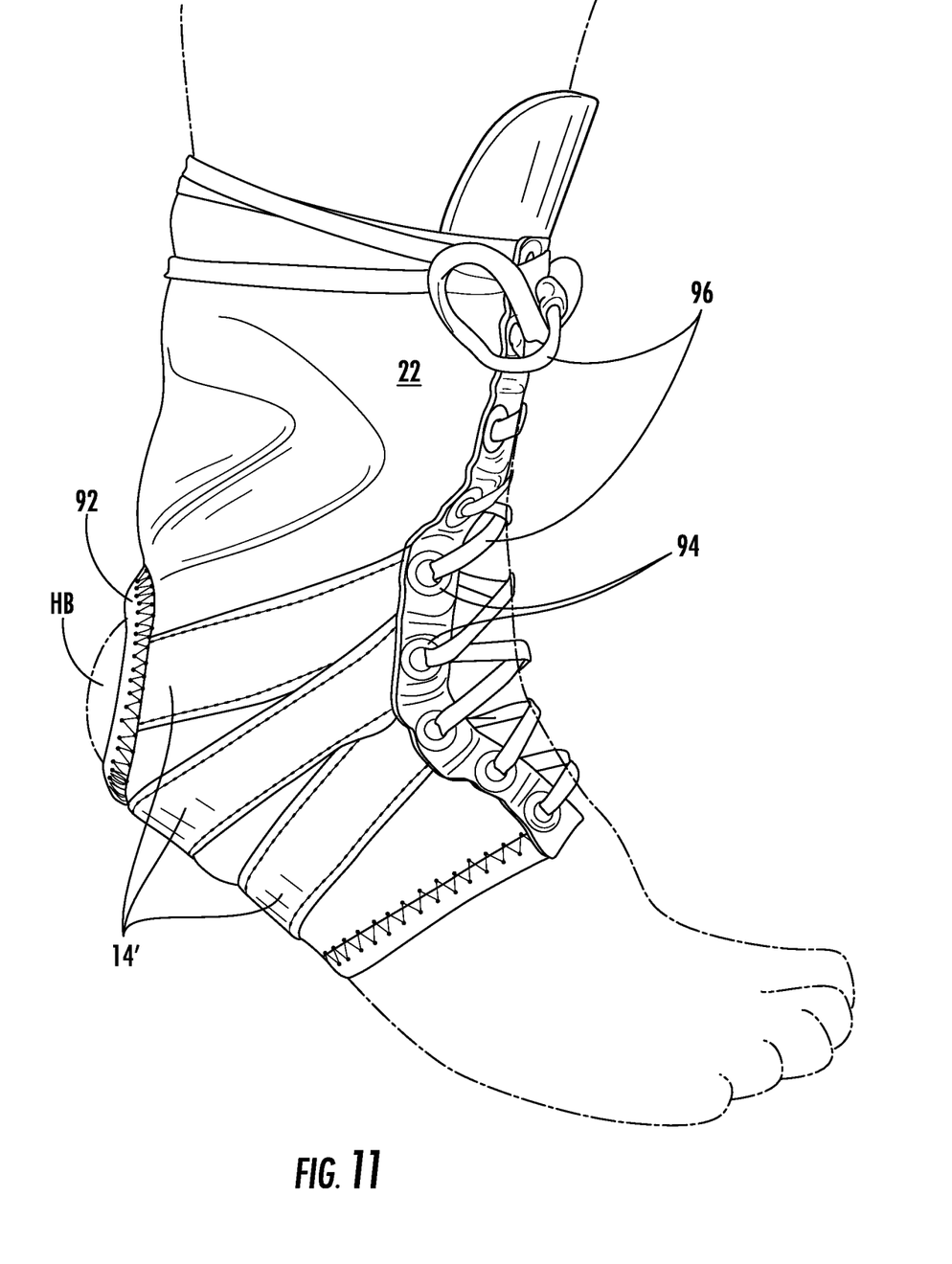
FIG. 11 shows the stabilizer of FIG. 10 applied to an ankle.

FIGS. 10 and 11 show an ankle stabilizer 90 according to the disclosure. The ankle stabilizer 90 is similar to the previously described stabilizers, but is configured to fit an ankle. The stabilizer 90 includes a web 12' formed of a plurality of flexible but substantially non-stretchable strips 14' interconnected in a desired pattern or arrangement depending on the desired effect. A plurality of non-adhesive and reusable flexible tacky strips 16' are located on the interior of the web 12' and aligned with and connected to at least selected ones of the non-stretchable strips 14'. The stabilizer 90 may also include an elastic textile 22' with the non-stretchable strips 14' and the tacky strips 16'. The textile 22' is configured to fit about the ankle joint and includes an aperture 92 for receiving the calcaneous or heel bone HB. The textile 22' may be provided as a compression sleeve or the textile 22 may be an open sleeve having closure structure, such as grommets 94 and a lace 96 for passage through the grommets and tying in the manner of a shoe lace.

The disclosure accordingly describes joint stabilizers that may be applied to a joint of the user to provide stability to the joint and a desired restriction in the range of motion of the joint. It is believed that the web 12 functions in the manner of taping and enables both mechanical and proprioceptive effects to the joint that are beneficial to rehabilitation of the joint. However, the web 12 advantageously may be removed and re-applied repeatedly and avoids disadvantages associated with taping.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

The invention claimed is:

1. A reusable joint stabilizer for application to a joint of a patient, the stabilizer comprising:
   a web having a pattern selected to provide a desired stability and restriction in the range of motion of the joint, the web being securable about the joint of the patient and formed of a plurality of flexible and non-stretchable strips interconnected in a desired pattern and a plurality of non-adhesive and reusable flexible tacky strips aligned with and connected to at least selected ones of the non-stretchable strips for positioning adjacent to skin of the patient proximate the joint;
   wherein the tacky strips transfer forces between the exterior of the web and the skin of the patient contacted by the tacky strips to provide a desired stability of the joint and a desired restriction in the range of motion of the joint.

2. The stabilizer of claim 1, further comprising an elastic textile configured to fit about the joint.

3. The stabilizer of claim 1, wherein the stabilizer comprises a shoulder stabilizer.

4. The stabilizer of claim 1, wherein the stabilizer comprises a prosthetic arm stabilizer.

5. The stabilizer of claim 1, wherein the stabilizer comprises an ankle stabilizer.

6. The stabilizer of claim 1, further comprising a secondary strap comprising an elastic section made of an elastic textile material connectable to a first portion of the joint stabilizer and a non-stretchable section connectable to a second portion of the joint stabilizer, wherein when the strap is installed about the joint, the elastic section of the strap is elongated and provides a compression force to the joint to add to the stability of the joint.

7. The stabilizer of claim 1, further comprising a belt and a supplemental strap, the belt being configured to be applied about a body portion of the patient remote from the joint, with the supplemental strap being configured to be connectable to the joint stabilizer and the belt and to extend therebetween to provide additional stability effects to the joint and further restrict the range of motion of the joint.

8. The stabilizer of claim 1, further comprising a belt and a supplemental strap, the belt being configured to be applied about a body portion of the patient remote from the joint, with the supplemental strap being configured to be connectable to the joint stabilizer and the belt and to extend therebetween to provide additional stability effects to the joint and further restrict the range of motion of the joint.

9. A reusable joint stabilizer for application to a joint of a patient, the stabilizer comprising:
   an elastic textile material configured to be secured about the joint;
   a web located on an exterior surface of the elastic textile material, the web having a pattern selected to provide a desired stability and restriction in the range of motion of the joint, the web being formed of a plurality of flexible and non-stretchable strips interconnected in a desired pattern; and
   a plurality of non-adhesive and reusable flexible tacky strips located on an interior surface of the elastic textile material; the tacky strips being aligned with and connected to at least selected ones of the non-stretchable strips for positioning adjacent to skin of the patient proximate the joint;
   wherein the tacky strips transfer forces between the exterior of the web and the skin of the patient contacted by the tacky strips to provide a desired stability of the joint and a desired restriction in the range of motion of the joint.

10. The stabilizer of claim 9, wherein the stabilizer comprises a shoulder stabilizer.

11. The stabilizer of claim 9, wherein the stabilizer comprises a prosthetic arm stabilizer.

12. The stabilizer of claim 9, wherein the stabilizer comprises an ankle stabilizer.

13. The stabilizer of claim 9, further comprising a secondary strap comprising an elastic section made of an elastic textile material connectable to a first portion of the joint stabilizer and a non-stretchable section connectable to a second portion of the joint stabilizer, wherein when the strap is installed about the joint, the elastic section of the strap is elongated and provides a compression force to the joint to add to the stability of the joint.

* * * * *